United States Patent
Mallikaratchy

(10) Patent No.: US 10,253,314 B2
(45) Date of Patent: Apr. 9, 2019

(54) LIGAND-GUIDED-SELECTION METHOD FOR SCREENING ANTIGEN-SPECIFIC LIGANDS

(71) Applicant: Research Foundation of the City University of New York, New York, NY (US)

(72) Inventor: Prabodhika Mallikaratchy, New York, NY (US)

(73) Assignee: Research Foundation of the City University of New York, New York, NY (US)

(*) Notice: Subject to any disclaimer, the term of this patent is extended or adjusted under 35 U.S.C. 154(b) by 171 days.

(21) Appl. No.: 15/097,845

(22) Filed: Apr. 13, 2016

(65) Prior Publication Data

US 2016/0298108 A1    Oct. 13, 2016

Related U.S. Application Data

(60) Provisional application No. 62/320,793, filed on Apr. 11, 2016, provisional application No. 62/253,963, filed on Nov. 11, 2015, provisional application No. 62/146,472, filed on Apr. 13, 2015.

(51) Int. Cl.
*C12N 15/10* (2006.01)
*G01N 33/53* (2006.01)
*C12N 5/07* (2010.01)

(52) U.S. Cl.
CPC ..... *C12N 15/1048* (2013.01); *G01N 33/5308* (2013.01)

(58) Field of Classification Search
CPC .................. C12N 15/1048; G01N 33/5308
See application file for complete search history.

(56) References Cited

U.S. PATENT DOCUMENTS

| 5,567,588 A | 10/1996 | Gold et al. |
| 5,861,254 A | 1/1999 | Schneider et al. |
| 6,127,119 A * | 10/2000 | Stephens ............... A61K 47/549 435/6.11 |
| 6,376,190 B1 | 4/2002 | Gold et al. |
| 2016/0003835 A1* | 1/2016 | Halbert ................ C12N 15/115 506/9 |

OTHER PUBLICATIONS

Ulrich et al. (J. Biol. Chem., 277(23):20756-20762) (Year: 2002).*
Kim et al. (Mol. Cells, 2014, 37(10):742-746) (Year: 2014).*
Ellington, A. et al; In Vitro selection of RNA molecules that bind specific ligands; nature; Aug. 30, 1990; pp. 818-822; vol. 346; Nature Publishing Group.

(Continued)

*Primary Examiner* — Jeremy C Flinders
(74) *Attorney, Agent, or Firm* — Peter J. Mikesell; Schmeiser, Olsen & Watts, LLP

(57) ABSTRACT

A Ligand-guided-Selection (LIGS) method for identifying highly specific aptamers against a predetermined antigen of a target is provided. LIGS uses a stronger and highly specific bivalent binder (e.g. an antibody) interacting with its cognate antigen to displace specific aptamers from a partially enriched SELEX pool. Elution of the displaced aptamers provides aptamers that are specific to the predetermined antigen.

8 Claims, 11 Drawing Sheets

Specification includes a Sequence Listing.

(56) References Cited

OTHER PUBLICATIONS

Burke, D. et al.; RNA aptamers to the adenosine moiety of S-adenosyl methionine: structural inferences from variations on a theme and the reproducibility of SELEX; Nucleic Acids Research; May 5, 1997; pp. 2020-2024; vol. 25, No. 10; Oxford University Press.

Shangguan, D. et al; Aptamers evolved from live cells as effective molecular probes for cancer study; PNAS; Aug. 8, 2006; pp. 11838-11843; vol. 103, No. 32; PMAS.

Theil, K. et al; Delivery of chemo-sensitizing siRNAs to HER2+- breast cancer cells using RNA aptamers; Nucleic Acids Research; Mar. 30, 2012; pp. 1-19.

Mayer, G. et al; Fluorescence-activated cell sorting for aptamer SELEX with cell mixtures; Nature Protocols; Dec. 2, 2010; pp. 1993-2004; vol. 5, No. 12; Nature America Inc.

Raddatz, M.L et al; Enrichment of Cell-Targeting and Population-Specific Aptamers by Fluorescence-Activated Cell Sorting; Angew. Chem. Int. Ed.; Jun. 3, 2008; pp. 5190-5193; vol. 47; Wiley-VCH Verlag GmbH & Co. KGaA.

Tang et al.; Selection of Aptamers for Molecular Recognition and Characterization of Cancer Cells; Analytical Chemistry; Jul. 1, 2007; pp. 4900-4907; vol. 79, No. 13; Americam Chemical Society.

Ye et al.; Generating Aptamers by Cell-SELEX for Applications in Molecular Medicine; International Journal of Molecular Sciences; Mar. 12, 2012; pp. 3341-3353; ISSN 1422-0067.

Mallikaratchy et al.; Aptamer Directly Evolved from Live Cells Recognizes Membrane Bound Immunoglobin Heavy Mu Chain in Burkitt's Lymphoma Cells; Molecular & Cellular Proteomics; Sep. 17, 2007; pp. 2230-2238; The American Society for Biochemistry and Molecular Biology, Inc.; US.

Sefah et al.; Development of DNA aptamers using Cell-SELEX; Nature Protocols; Jun. 3, 2010; pp. 1169-1185; vol. 5 No. 6; Nature Publishing Group; US.

Wilner et al.; An RNA Alternative to Human Transferrin: A New Tool for Targeting Human Cells; Molecular Therapy—Nucleic Acids; May 15, 2012; pp. 1-14; American Society of Gene & Cell Therapy; US.

\* cited by examiner

FIG. 5

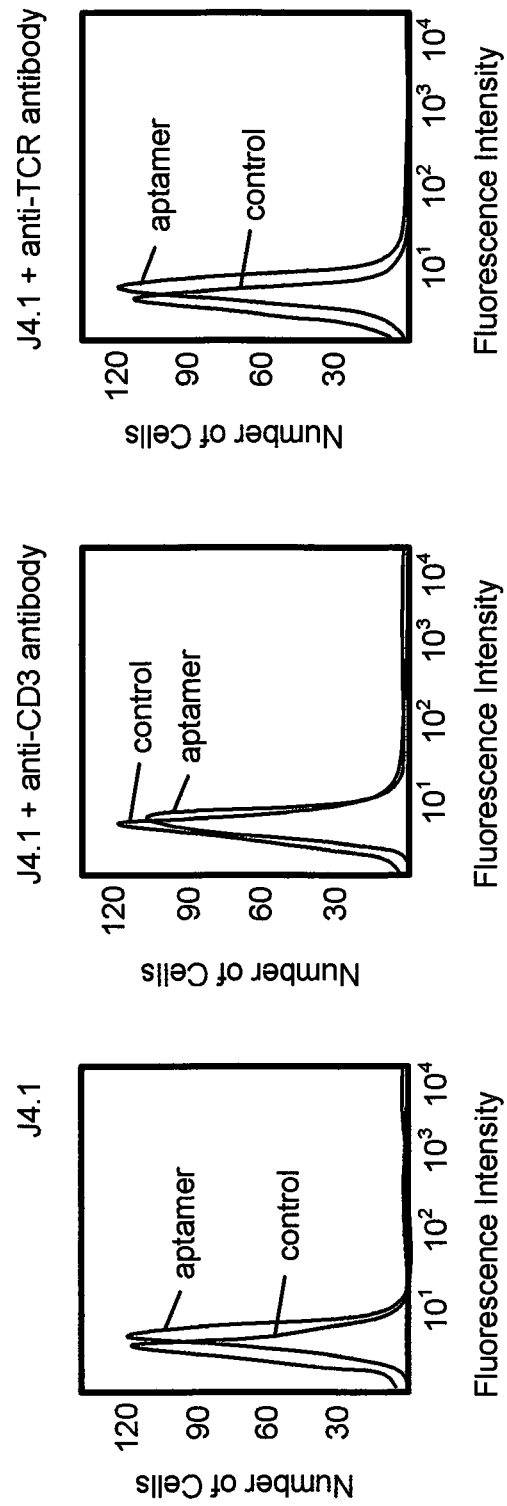

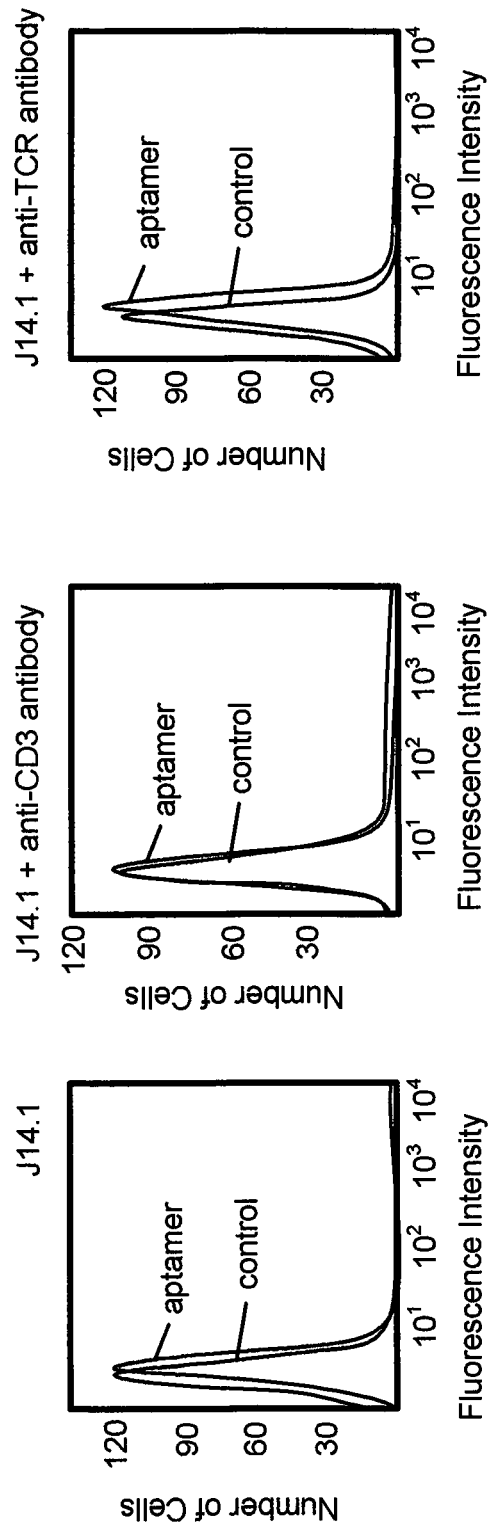

FIG. 7

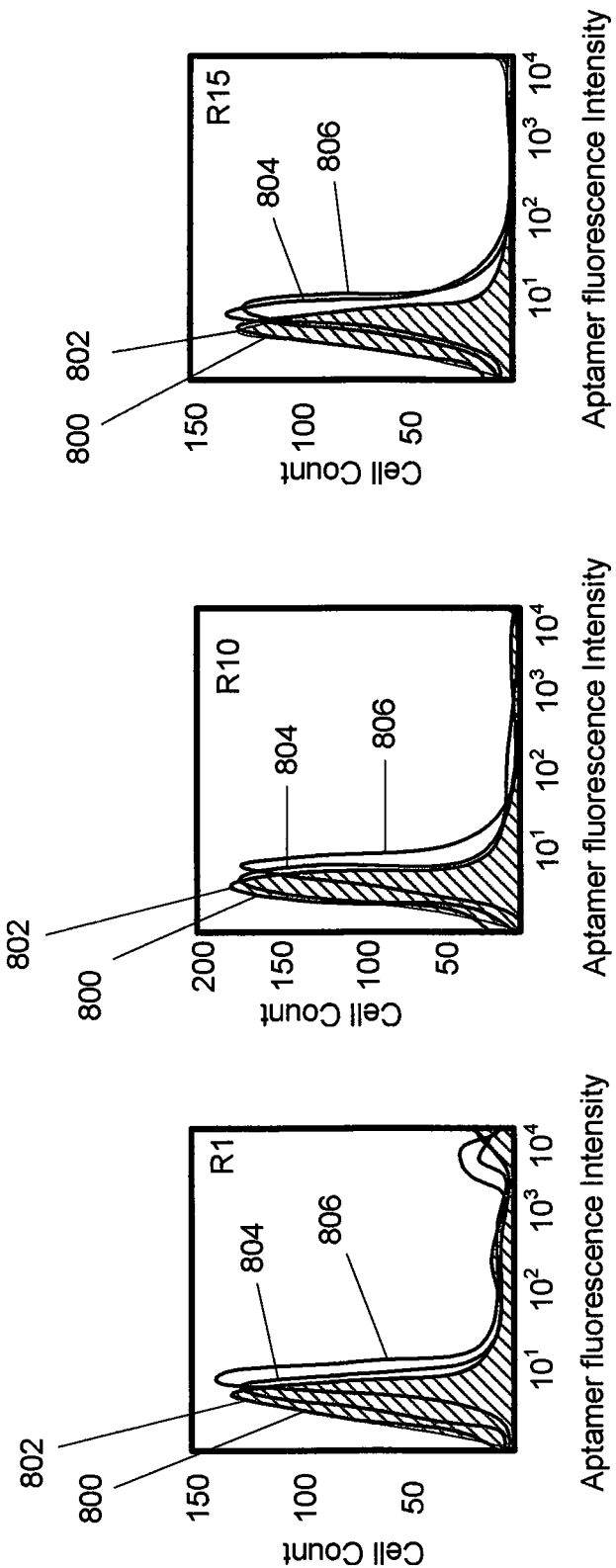

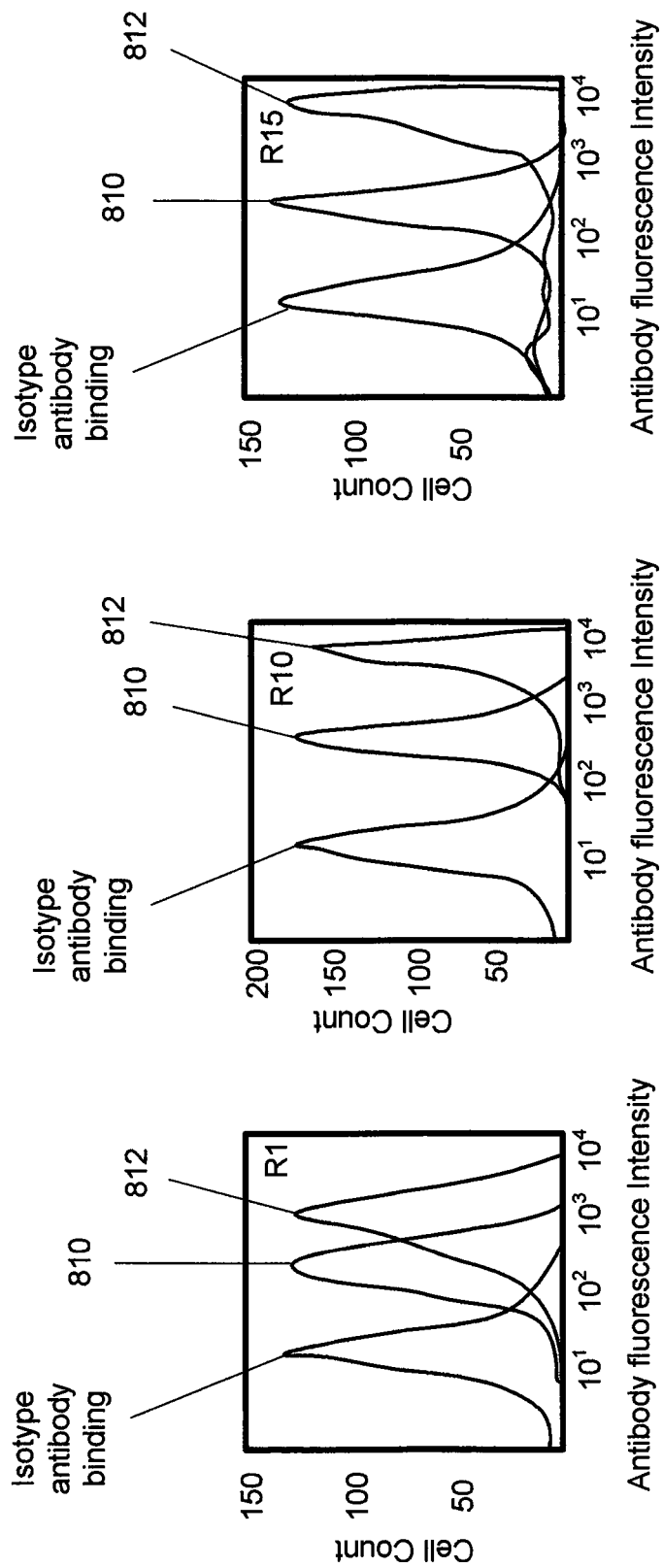

```
                        SEQUENCE LISTING

<160> NUMBER OF SEQ ID NOS: 17

<210> SEQ ID NO 1
<211> LENGTH: 45
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 1
tcggtctgtc tctatctatg ggaggtaaga actttgttcc tgatt              45

<210> SEQ ID NO 2
<211> LENGTH: 41
<212> TYPE: DNA
<213> ORGANISM: Artificial Sequence
<220> FEATURE:
<223> OTHER INFORMATION: Completely synthetic sequence from SELEX
      library.

<400> SEQUENCE: 2
gttagggtgt gtcgtcgtgg taaggagcag cgtggaggat a                  41

<210> SEQ ID NO 3
<211> LENGTH: 40
<212> TYPE: DNA
<213> ORGANISM: Artificial Sequence
<220> FEATURE:
<223> OTHER INFORMATION: Completely synthetic sequence from SELEX
      library.

<400> SEQUENCE: 3
ttagggtgtg tcgtcgtggt aaggagcagc gtggaggata                    40

<210> SEQ ID NO 4
<211> LENGTH: 80
<212> TYPE: DNA
<213> ORGANISM: Artificial Sequence
<220> FEATURE:
<223> OTHER INFORMATION: Completely synthetic sequence from SELEX
      library.

<400> SEQUENCE: 4
gtacactagt tatgtcccgg gtcgacatca ctgtagcggc gtcagttagg gtgtgtcgtc  60
gtggtactcg tggtgccgcc                                             80

<210> SEQ ID NO 5
<211> LENGTH: 21
<212> TYPE: DNA
<213> ORGANISM: Artificial Sequence
<220> FEATURE:
<223> OTHER INFORMATION: Completely synthetic sequence identified by
```

LIGS from SELEX library.

<400> SEQUENCE: 5
gttagggttt gtcgtcgtgg t                                              21

<210> SEQ ID NO 6
<211> LENGTH: 38
<212> TYPE: DNA
<213> ORGANISM: Artificial Sequence
<220> FEATURE:
<223> OTHER INFORMATION: Completely synthetic sequence from SELEX
      library.

<400> SEQUENCE: 6
ttagggtgtg tcgtcgtggt aaggggtta atgaggtg                             38

<210> SEQ ID NO 7
<211> LENGTH: 45
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 7
aaagttagct gtttcctcgt ggcagaagga acagaccacc gtact                    45

<210> SEQ ID NO 8
<211> LENGTH: 45
<212> TYPE: DNA
<213> ORGANISM: Artificial Sequence
<220> FEATURE:
<223> OTHER INFORMATION: Completely synthetic sequence from SELEX
      library.

<400> SEQUENCE: 8
tcggtaaggg tcggggatgc tacaactgtt taaacgaccc gtcca                    45

<210> SEQ ID NO 9
<211> LENGTH: 45
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 9
atttaaaaca tgaggatacg aacccgtacc gctgagacgt gacca                    45

<210> SEQ ID NO 10
<211> LENGTH: 27
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 10
cgaacccgta ccgctgagac gtgacca                                        27

<210> SEQ ID NO 11
<211> LENGTH: 43
<212> TYPE: DNA
<213> ORGANISM: Artificial Sequence
<220> FEATURE:
<223> OTHER INFORMATION: Completely synthetic sequence from SELEX
      library.

```
<400> SEQUENCE: 11
cattatacca caaagtcgtg agttaagtta gtagcagacc tat          43

<210> SEQ ID NO 12
<211> LENGTH: 51
<212> TYPE: DNA
<213> ORGANISM: Artificial Sequence
<220> FEATURE:
<223> OTHER INFORMATION: Completely synthetic sequence from SELEX
      library.

<400> SEQUENCE: 12
tcccatggcc tctaacttcc aaacatacca catttaacat gaacccaact g    51

<210> SEQ ID NO 13
<211> LENGTH: 43
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 13
aacactgggt ggggttagcg ggcgatttag ggatcttgac tgg          43

<210> SEQ ID NO 14
<211> LENGTH: 42
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 14
cgccggtgtt gacgaaacgg gatggggagc gcggggaccg ga           42

<210> SEQ ID NO 15
<211> LENGTH: 43
<212> TYPE: DNA
<213> ORGANISM: Artificial Sequence
<220> FEATURE:
<223> OTHER INFORMATION: Completely synthetic sequence identified by
      LIGS from SELEX library.

<400> SEQUENCE: 15
gggtggagag gtggaggcgt ggagagaacg ggaaggctca gca          43

<210> SEQ ID NO 16
<211> LENGTH: 10
<212> TYPE: DNA
<213> ORGANISM: Artificial Sequence
<220> FEATURE:
<223> OTHER INFORMATION: Completely synthetic sequence from SELEX
      library.

<400> SEQUENCE: 16
ggataggggg                                               10

<210> SEQ ID NO 17
<211> LENGTH: 51
<212> TYPE: DNA
<213> ORGANISM: Artificial Sequence
<220> FEATURE:
```

-continued

```
<223> OTHER INFORMATION: Completely synthetic sequence identified by
      LIGS from SELEX library.

<400> SEQUENCE: 17
ctaaacagaa ggggtcggtc ggtctggcgc ggacctcgag tcatggtggg t        51
```

LIGAND-GUIDED-SELECTION METHOD FOR SCREENING ANTIGEN-SPECIFIC LIGANDS

CROSS-REFERENCE TO RELATED APPLICATIONS

This application claims priority to and is a non-provisional of U.S. Patent Application Ser. 62/146,472 (filed Apr. 13, 2015); U.S. Patent Application 62/253,963 (filed Nov. 11, 2015) and U.S. Patent Application 62/320,793 (filed Apr. 11, 2016) the entirety of which are incorporated herein by reference.

STATEMENT OF FEDERALLY SPONSORED RESEARCH OR DEVELOPMENT

This invention was made with government support under contract number SC3GM105578 awarded by the National Institute of Health (NIH). The government has certain rights in the invention.

REFERENCE TO A SEQUENCE LISTING

This application refers to a "Sequence Listing" listed below, which is provided as an electronic document entitled "RESE17305RO_ST25.txt" (5 kb created on Apr. 12, 2016) which is incorporated herein by reference in its entirety.

BACKGROUND OF THE INVENTION

The subject matter disclosed herein relates to methods for screening for an aptamer. Aptamers are small synthetic nucleic acid strands that specifically bind to a target molecule with high affinity. One conventional method of aptamer selection is known as SELEX (Systematic Evolution of Ligands by Exponential enrichment). SELEX allows the screening of oligonucleotides against a variety of target ligands via an iterative and evolutionary process of continuous enrichment to identify target-specific binders. A typical SELEX library is vastly heterogeneous with a large number of distinct nucleic acid molecules (approximately $10^{13}$ molecules). Each molecule folds into a unique secondary structure, which leads to a distinct geometrical shape. Depending on shape complementarity and non-covalent electrostatic or hydrophobic interactions, a few DNA sequences can specifically bind to the desired target. Subsequently, bound sequences are separated and amplified using Polymerase Chain Reaction (PCR) to generate an evolved library. The process is repeated until high-affinity binders are enriched, resulting in a homogeneous library with high-affinity nucleic acid aptamers against the target of interest. SELEX has resulted in generating a significant number of aptamers against targets ranging from small molecules to whole cells; however, translational applications have been limited. To increase the clinical practicality of aptamer selection, development of methods to identify aptamers that could specifically recognize predetermined antigens in their endogenous state with no prior- or post SELEX sample manipulations on receptor proteins is desirable.

The discussion above is merely provided for general background information and is not intended to be used as an aid in determining the scope of the claimed subject matter.

BRIEF DESCRIPTION OF THE INVENTION

A "Ligand-guided-Selection" (LIGS) method for identifying highly specific aptamers against a predetermined antigen of a target is provided. LIGS uses a stronger and highly specific binder (e.g. an antibody) interacting with its cognate antigen to displace specific aptamers from a partially enriched SELEX pool. Elution of the displaced aptamers provides aptamers that are specific to the predetermined antigen. An advantage that may be realized in the practice of some disclosed embodiments of the method is that it enables identification of one or more aptamers that is specific to a predetermined antigen on a given cell line.

In a first embodiment, a Ligand-guided-Selection method for screening ligands that are specific to an antigen is provided. The method comprises sequential steps of forming a ligand-cell complex by exposing a culture of target cells to a library of ligands, wherein cells in the culture of target cells each have an antigen; treating the ligand-cell complex with a predetermined ligand that is specific to the antigen, the predetermined ligand displacing ligands that are bound to the antigen to form displace ligands; eluting the displaced ligands; and amplifying the displaced ligands.

In a second embodiment, a Ligand-guided-Selection method for screening ligands that are specific to an antigen is provided. The method comprises sequential steps of constructing a library of ligands by exposing a target cell line to an aptamer library and permitting at least some aptamers to bind to the target cell line, thereby forming bound aptamers; removing aptamers that do not bind to the target cell line; eluting the bound aptamers, thereby forming eluted aptamers; amplifying the eluted aptamers that are specific to the cell line, thereby forming the library of ligands. A ligand-cell complex is formed by exposing a culture of target cells to the library of ligands, wherein cells in the culture of target cells each have an antigen; treating the ligand-cell complex with an antibody that is specific to the antigen, the antibody displacing ligands that are bound to the antigen to form displace ligands; eluting the displaced ligands; amplifying the displaced ligands.

In a third embodiment, a method for selecting aptamers using an antibody-capped cell Systematic Evolution of Ligands by EXponential enrichment process is provided. The method comprising steps of exposing an antibody-capped cell to a plurality of different aptamers and permitting at least some aptamers to bind to the antibody-capped cell to form bound aptamers, wherein the antibody-capped cell has been pretreated with an antibody that caps an antigen; eluting unbound aptamers; and amplifying the unbound aptamers.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a sequence alignment showing patterns in aptamers identified by LIGS for CD3ε expressed on T lymphocytes compared to select aptamers from the SELEX pool;

FIG. 6D, FIG. 6E and FIG. 6F are flow cytometric competitive binding analysis of J4.1 without anti-CD3ε (FIG. 6D), with anti-CD3ε (FIG. 6E) and anti-TCRαβ antibody (FIG. 6F);

FIG. 6G, FIG. 6H and FIG. 6I are flow cytometric competitive binding analysis of J14.1 without anti-CD3ε (FIG. 6G), with anti-CD3ε (FIG. 6H) and anti-TCRαβ antibody (FIG. 6I);

FIG. 7 is a sequence alignment showing patterns in aptamers identified by LIGS for IgM expressed on Burkitt's lymphoma cells compared to select aptamers from the SELEX pool;

FIG. 8A, FIG. 8B and FIG. 8C depict the results of flowcytometric competitive binding analysis of R1, R10 and R15, respectively, in the presence of IgM or in the presence of anti-CD20; and FIG. 8D, FIG. 8E and FIG. 8F show anti-IgM and anti-CD20 Ab on the binding of the aptamer for with Ramos cells during competition experiments with R1 (FIG. 8D), R10 (FIG. 8E) and R15 (FIG. 8F).

DETAILED DESCRIPTION OF THE INVENTION

Figure 1:
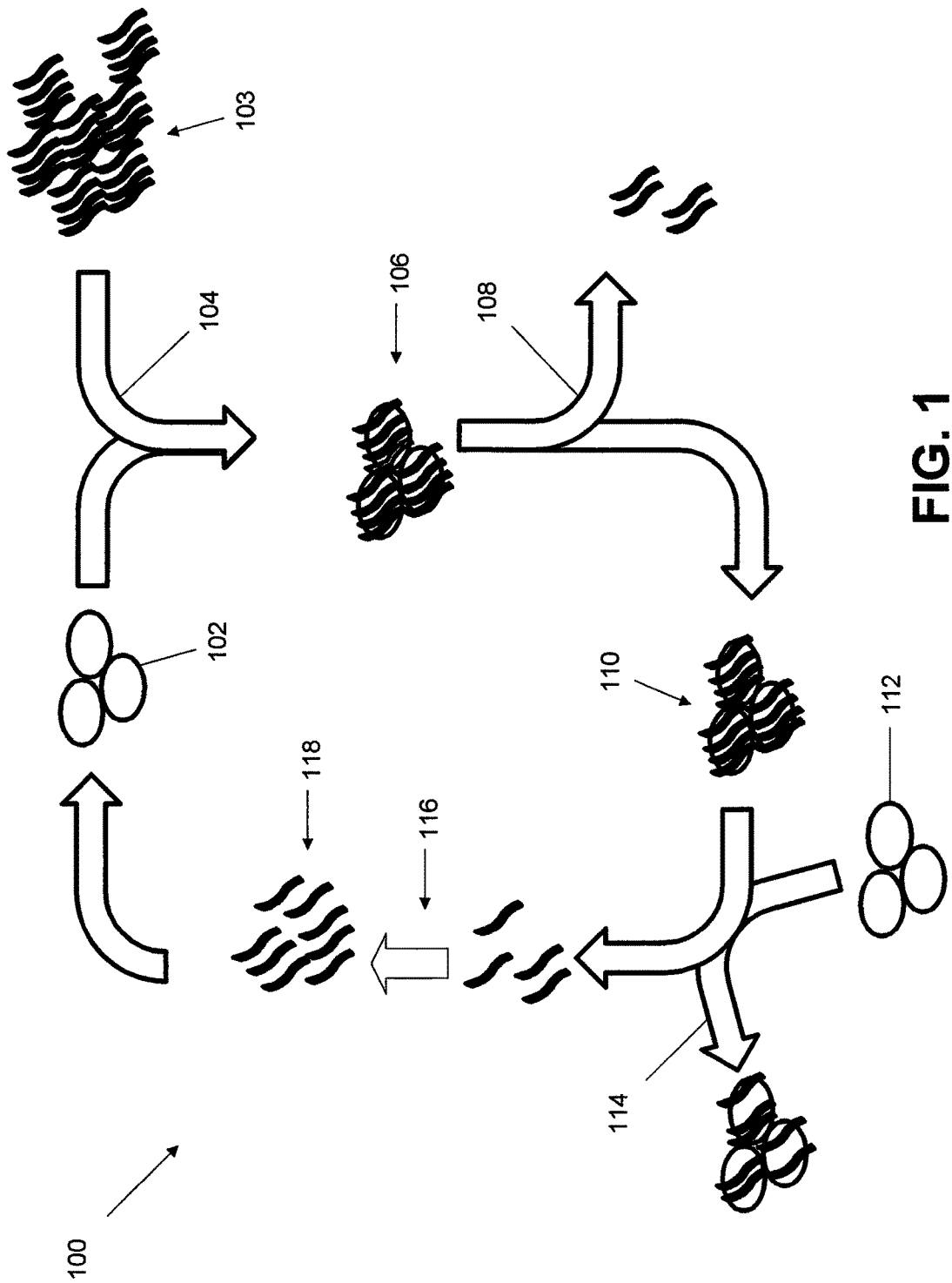
FIG. 1 is a schematic flow diagram of a cell-SELEX method.

Disclosed in this specification is a method referred to as Ligand-guided Selection, (LIGS), which allows identification of aptamers specific for a predetermined antigen expressed on a cell surface. LIGS interrupts the cell-SELEX process at the stage of enrichment of a SELEX library and introduces a secondary, pre-existing ligand (e.g. an antibody) to outcompete and elute aptamers specific for the membrane receptor of the secondary ligand. LIGS introduces a stronger, known high-affinity ligand against the target of interest to achieve two purposes: 1) to directly outcompete and replace aptamers specific towards the antigen of interest and 2) to introduce structural changes on the target protein upon binding of the ligand to outcompete specific aptamers. Based on the specificity of the ligand towards its antigen, the aptamers identified by LIGS show higher specificity towards the antigen than those succeeding as cell-specific binders via cell-SELEX.

The cell-SELEX method allows the selection of aptamers towards membrane receptor targets in their native state at their endogenous levels with no prior requirement for the overexpression of a protein. Nevertheless, proteomic identification of the receptor protein ligand of aptamers generated from cell-SELEX is a challenge. With such limitation, therapeutic and diagnostic applications of aptamers remain challenging. Therefore, to address this challenge, LIGS is introduced as a simple technique to selectively separate aptamers binding to a specific antigen using a ligand specific to the same antigen. From a fundamental point-of view, LIGS technology pushes separation efficiency to a remarkably high level. That is, the competition strategy allows us to separate out a few aptamer molecules that bind to a specific antigen of a specific receptor molecule in its endogenous state from a complex library evolved against a whole cell. Since the aptamers selected using LIGS are selectively eluted based on the interaction of the ligand with its target antigen at its endogenous state, LIGS-generated aptamers have higher potential in identifying same antigen in a clinical setting. Moreover, apart from selecting aptamers against antigens in a multidomain protein complex, LIGS can be applied to a number of platforms, such as aptamer binding toward active sites of an enzyme, utilizing the enzyme substrate as a guide, or growth factor binding sites, utilizing growth factor interacting with receptor protein as a guide, hormones and signaling molecules that trigger protein conformation e.g. GPCR family of receptors. Aptamers can also be selected toward a small-molecule ligand-binding site, utilizing small-molecule ligand-receptor interaction as a guide. That LIGS can identify aptamers against one single domain of a multidomain system demonstrates the significance of LIGS in generating highly specific nucleic acid ligands toward a broader range of receptor molecules already characterized as surface markers. This approach can be extended to a number of combinatorial screening platforms, including phage-display libraries and small-molecule libraries.

A schematic depiction of a traditional cell-SELEX method 100 is shown in FIG. 1. Cells 102 are subjected to an incubation and selection step 104 wherein the cells 102 are exposed to a SELEX library 103 of aptamers. A select number of these aptamers bind to the cells 102 to form a bound complex 106. Unbound aptamers are removed in washing step 108 to leave a washed, bound complex 110. The washed, bound complex 110 is exposed to cells 112 that are different than the cells 102. Bound aptamers competitively bind to either the cells 102 or the cells 112 such that aptamers with a low binding affinity for the cells 102 can accumulate on the cells 112 and can be removed in step 114. High binding affinity aptamers remain on the cells 102 and are subsequently eluted to provide isolated aptamers 116. PCR may be used to amplify the resulting aptamers and, in this fashion, an evolved cell-SELEX library 118 is constructed. The resulting evolved cell-SELEX library 118 is specific for the cells 102.

Figure 2:
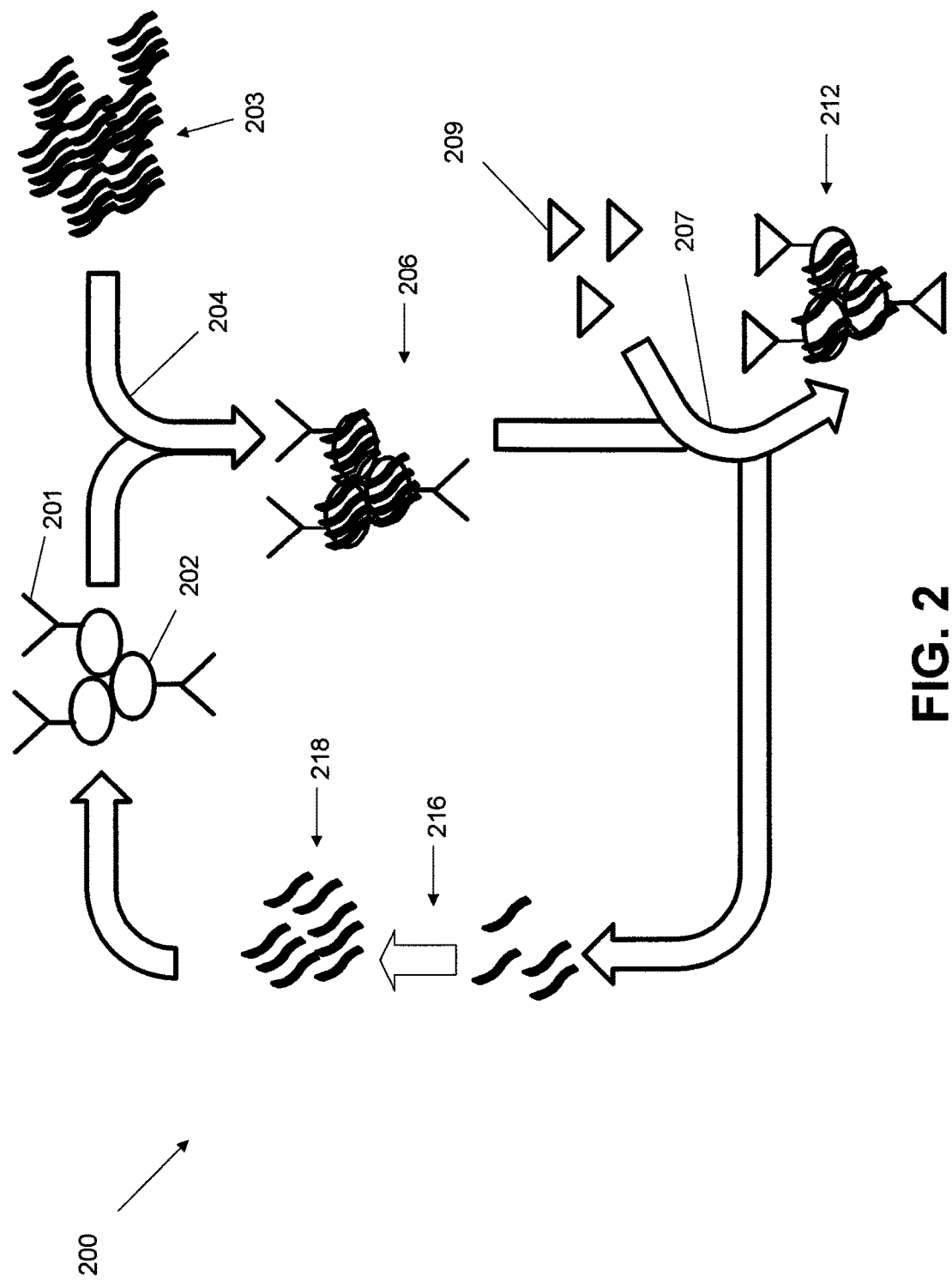
FIG. 2 is a schematic flow diagram of a LIGS method.

A schematic depiction of a LIGS method 200 is shown in FIG. 2. Positive cells 202 that are positive for a target antigen 201 are subjected to an incubation and selection step 204 wherein the positive cells 202 are exposed to a SELEX library 203 of aptamers. In one embodiment, the SELEX library of aptamers has been pre-screened using a conventional SELEX method (e.g. cell-SELEX). A select number of these aptamers bind to the positive cells 202 to form a bound complex 206.

In step 207 the bound complex 206 is exposed to a high affinity ligand 209 that is known to preferentially bind to the target antigen 201 to form a ligand-cell complex 212. Examples of high affinity ligands include antibodies, small organic molecules and ions. In one embodiment, the high-affinity ligand has a molecular weight of greater than 200,000 g per mole. In another embodiment, the high affinity ligand is a small molecule with molecular weight greater than 400 g per mol. In another embodiment, the high affinity ligand is an ion with molecular weight greater than 1 g per mol. This binding displaces high binding affinity aptamers 216 while leaving other aptamers bound to the ligand-cell complex 212. In one embodiment, the displacement occurs through a competitive displacement mechanism where binding occurs at the same epitope of the antigen. In another embodiment, the displacement occurs due to a conformational change in the antigen that is induced by the binding of the high binding affinity aptamers 216 at a location other than the epitope of the antigen. The high binding affinity ligand 209 are added in excess relative to the antigen 201. In one embodiment at least a two-fold molar excess is used. In another embodiment, at least a five-fold excess is used. In yet another embodiment, at least a ten-fold molar excess is used. The high affinity binding aptamers 216 are eluted to separate them from the ligand-cell complex 212 and any aptamers bound thereto.

PCR may be used to amplify the resulting high binding affinity aptamers 216 and, in this fashion, a library 218 is constructed. The library 218 are aptamers that are specific to the target antigen 201 which are subset of the aptamers that are specific to positive cells 202. In one embodiment, the LIGS method 200 is repeated one or more times to further refine the number of aptamers in the resulting library. The resulting aptamers may then be isolated by conventional methods.

Figure 3:
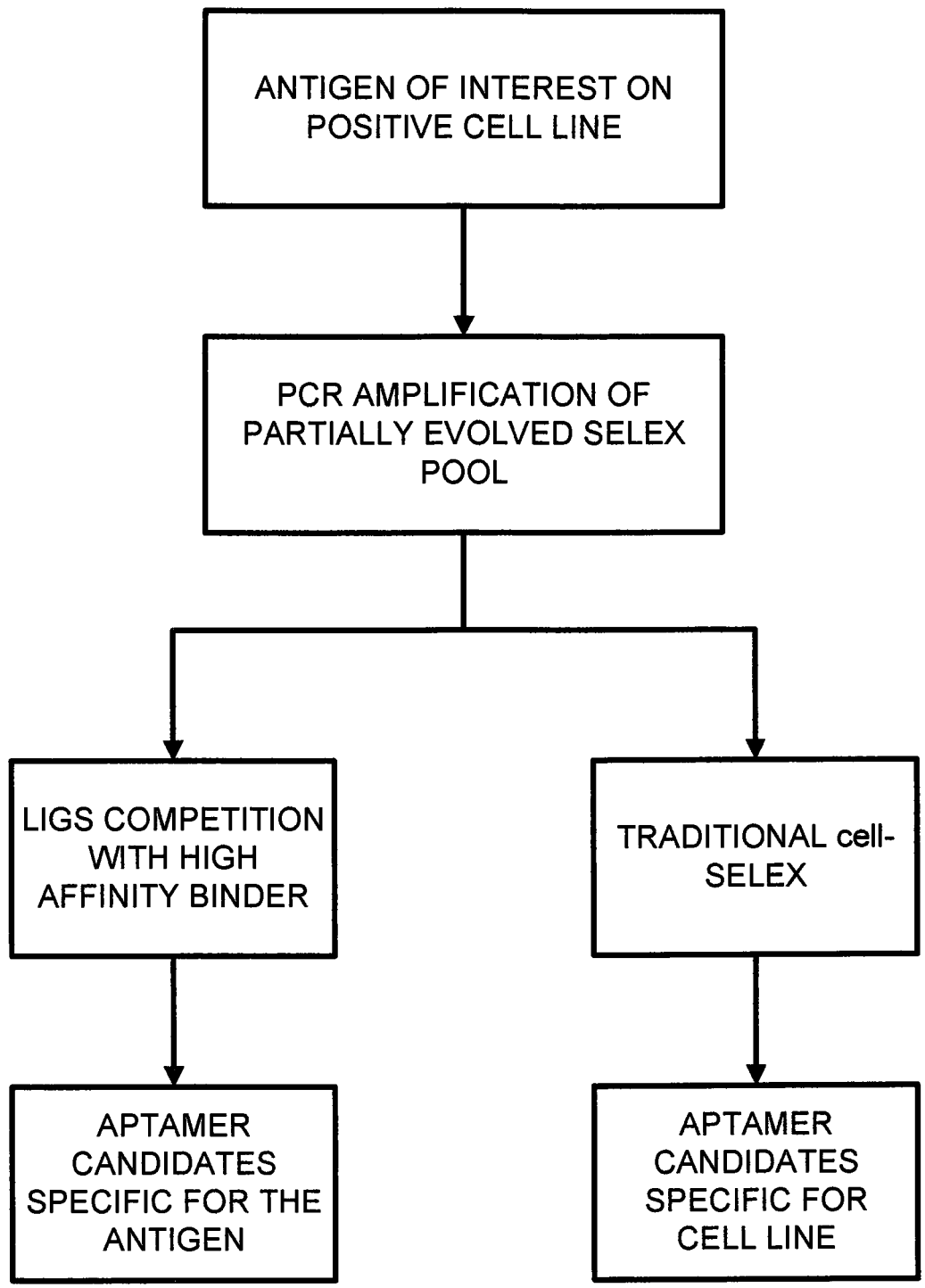
FIG. 3 is a schematic comparison of outputs of cell-SELEX and LIGS.

As graphically depicted in FIG. 3, the traditional cell-SELEX methodology provides aptamers that are specific for a given cell line. In contrast, the disclosed LIGS methodology provides aptamers that are specific for a given antigen.

Figure 4:
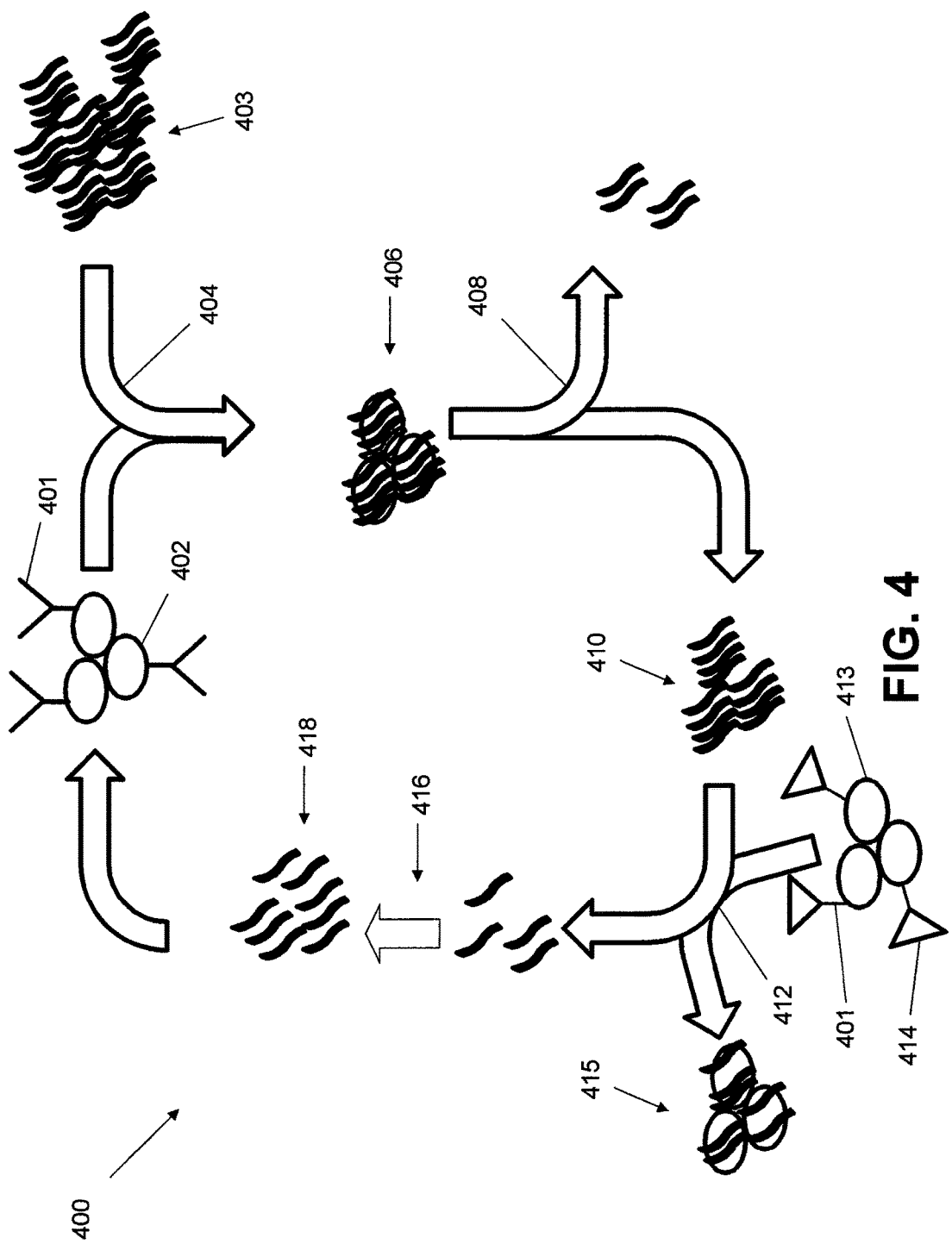
FIG. 4 is a schematic flow diagram of a LIGS method that uses antibody capping.
Figure 6C:
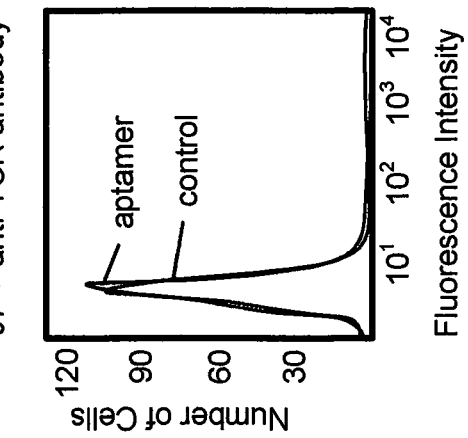
FIG. 6A, FIG. 6B and FIG. 6C are flow cytometric competitive binding analysis of J7 without anti-CD3ε (FIG. 6A), with anti-CD3ε (FIG. 6B) and anti-TCRαβ antibody (FIG. 6C)
Figure 6B:
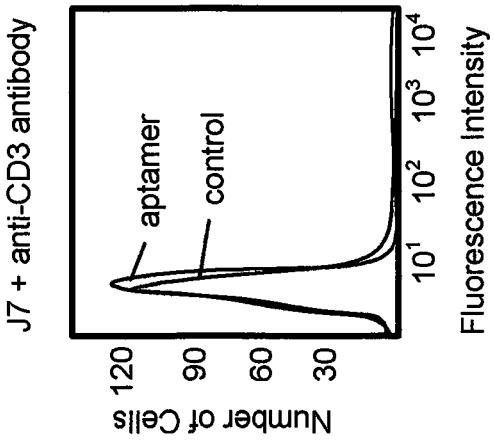
Figure 6A:
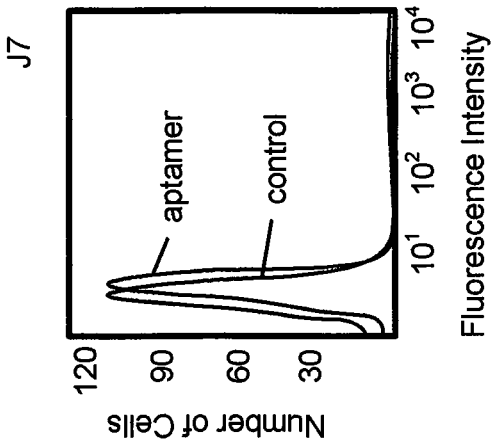

FIG. 4 depicts an antibody capped method 400. Positive cells 402 that are positive for a target antigen 401 are subjected to an incubation and selection step 404 wherein the positive cells 402 are exposed to a SELEX library 403 of aptamers. In one embodiment, the SELEX library of aptamers has been pre-screened using a conventional SELEX method (e.g. cell-SELEX). A select number of these aptamers bind to the positive cells 402 to form a bound complex 406. Unbound aptamers are removed in washing step 408 and bound aptamers are subsequently eluted to produce partially screened aptamers 410.

In step 412 the partially screened aptamers 410 are exposed to cells 413. Cells 413 are positive for antigen 401 but antigen 401 has been capped with antibody 414. Aptamers bind to the cell 413 to form complex 415 and thereby selectively remove aptamers except for aptamers 416 which are prevented from binding due to the presence of antibody 414. PCR may be used to amplify the resulting high binding affinity aptamers 416 and, in this fashion, a library 418 is constructed. The library 418 are aptamers that are specific to the target antigen 401 which are subset of the aptamers that are specific to positive cells 402.

In one embodiment, a sequence alignment strategy is used to identify aptamer sequences that were not identified by LIGS but are (1) structurally similar to aptamers identified by LIGS and (2) were identified by SELEX. Sequences obtained from sequencing cell-SELEX pool and sequences obtained from LIGS pools are aligned to identify aptamer candidates specific for the antigen. This alignment strategy is design to address/identify aptamers that might not be outcompeted by a secondary ligand but binding to same surface marker. By aligning multiple pools similar aptamer sequences belonging to the same family are shown. If the sequence repeated multiple times in LIGS library this is considered an indication that the repeated sequence may be a desirable aptamer. In one such embodiment, the sequence is repeated at least four times. If a sequence show segments of bases spanning 5 bases to 10 bases from either library that sequence is a hit.

EXAMPLE 1

CD3ε Expressed on T Lymphocytes

LIGS was used to identify aptamers against CD3ε expressed on T lymphocytes from a partially enriched SELEX library against a whole cell. CD3ε is one of the ectodomains of the T-cell receptor (TCR) complex expressed on T-cells. Using high-affinity anti-CD3 antibody against a specific antigen on the CD3ε chain as the secondary ligand, three specific aptamers against CD3ε domain were successfully identified.

The expression of CD3ε on Jurkat.E6 cells was confirmed by flow cytometry using a fluorescently labeled anti-CD3ε antibody. The selection library had 45 randomized nucleotides flanked by two primers, but with modifications pertaining to the conditions for PCR were further optimized to ensure high PCR efficiency of the library. The first round of cell-SELEX employed approximately 7 million Jurkat.E6 cells to ensure that all potential binders were retained. A total of 5 million cells were then used during the second round of selection, and the number of cells used in cell-SELEX was decreased to 2.5 million cells in subsequent rounds to increase the stringency of the selection. Enrichment at round 16 of cell-SELEX against the Jurkat.E6 cells was observed. At this point, cell-SELEX was stopped, and LIGS was introduced to a fraction of round 16 from cell-SELEX.

For the first step of LIGS, a total of $1 \times 10^5$ Jurkat.E6 cells were prewashed with wash buffer and incubated 40 minutes with 6.25 pmols of round 16 of cell-SELEX. After incubation, cells were washed twice, first with 1 mL wash buffer and then 0.5 mL wash buffer to remove unbound DNA molecules. Next, cells were reconstituted in 50 μl, cell binding buffer, and 2.5 μL of anti-CD3ε HIT3 clone were added. Competitive elution of CD3ε-specific aptamers by the antibody was allowed for 40 minutes on ice. Following incubation, cells were spun down, and supernatant containing competitively eluted aptamers was collected.

Cells were analyzed after LIGS to investigate whether the addition of antibody had affected the binding of round 16 of cell-SELEX. The addition of the antibody had, indeed, replaced some aptamers from that round, as indicated by the slight decrease of fluorescence intensity. Interaction of anti-CD3ε HIT3a clone with CD3ε on Jurkat.E6 cells was also confirmed.

Figure 5:
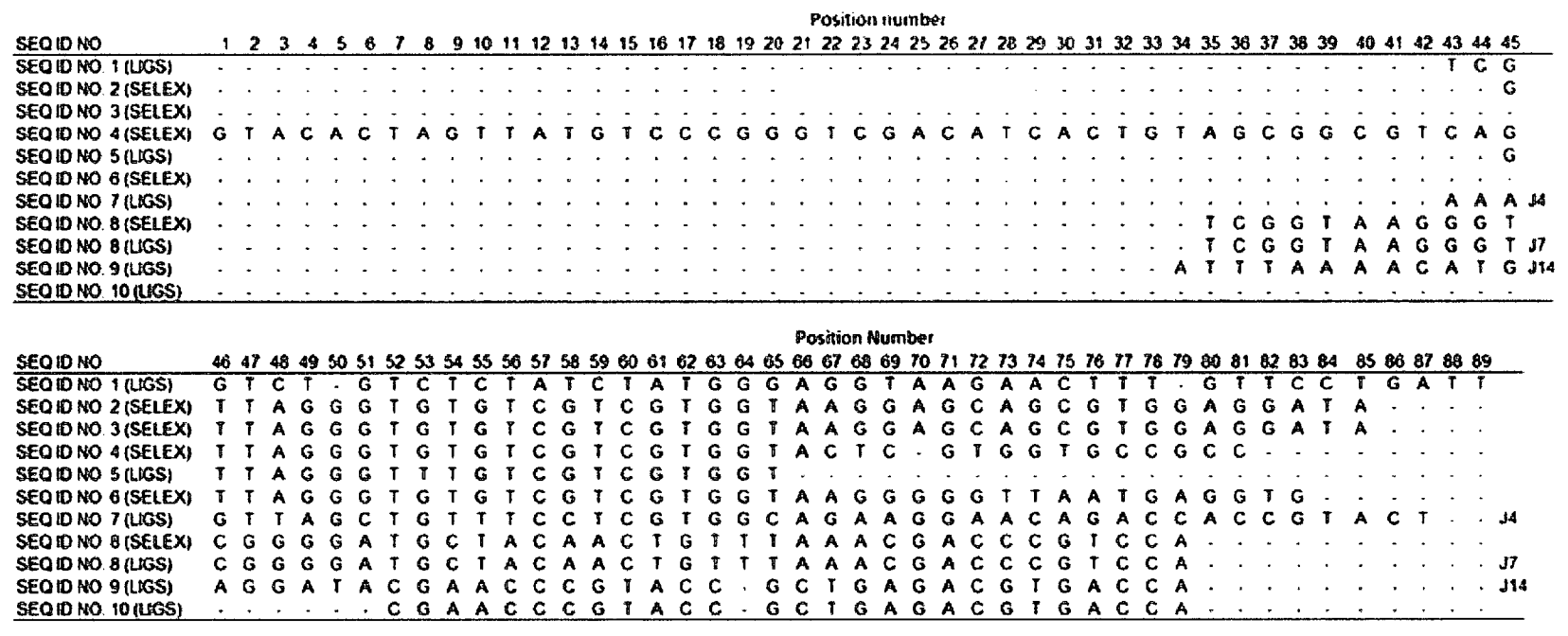

Sequence alignment strategy: The supernatant containing competitively eluted potential DNA molecules from LIGS were then PCR-amplified. To ensure that all copies of competitively eluted potential DNA aptamers were adequately amplified, a two-step PCR process was conducted. Two libraries, including (1) round 16 of cell-SELEX, which had sequences enriched towards the whole cell target, and (2) competitively eluted pool, consisting of sequences specific for CD3ε from LIGS, were cloned into bacterial vector using TOPO TA cloning and subjected to DNA sequencing. Sequences were analyzed using ClustalX.2. Analysis revealed multiple copies of the same sequences, or repeated common shared motifs interrupted by segments of DNA bases unique to each sequence. See FIG. 5. Alignment was performed on the competitively eluted sequences from LIGS and sequences from round 16 of cell-SELEX containing all sequences evolved towards Jurkat.E6 cells. Three homologous patterns were observed between the two libraries: 1) repetition of the same sequences within the pool unique to the respective libraries; 2) repetition of the same sequences in both competitively eluted library and round 16 of cell-SELEX library; and 3) repetition of sequences with common motifs in both libraries. In the case of 3), even though sequences were derived from two different pools, they shared a common motif, differing only by a few bases. Without wishing to be bound to any particular theory, it is believed that specifically enriched sequences towards the Jurkat.E6 cell line would dominate the library and that after subsequent cloning and DNA sequencing steps, these sequences would still predominate such that round 16 of cell-SELEX library would contain all sequences enriched towards Jurkat.E6 cells. Very importantly, however, the sequences obtained from LIGS would favor the selectively eluted sequences by anti-CD3 antibody binding to CD3ε antigen. Therefore, the sequences that repeatedly appeared within a family with common motifs from the two different pools were deemed more significant. Since the objective of this example aimed to select only the aptamers with most binding specificity based on LIGS, only the sequences competitively eluted by anti-CD3ε antibody sharing common motifs within the library or with round 16 of cell-SELEX library were selected for synthesis. Based on the sequence alignment, twenty seven sequences were selected for further study.

Accordingly, a total of twenty seven individual sequences were synthesized with FAM-dT at the 3'-end using standard phosphoramidite solid-state synthesis, followed by reversed phase HPLC purification. Specific binding of the sequences was tested against Jurkat.E6, using Burkitt's lymphoma cell line Ramos as the negative cell line. Burkitt's lymphoma stems from B-cell lineage, which does not express TCR-CD3 complex. A 1 µM solution of respective aptamers against $75-100\times10^4$ cells was incubated for 1 hour at 4° C. and subsequently washed twice with wash buffer prior to flow cytometric analysis for binding.

Interestingly, out of the twenty seven tested sequences, three sequences, J4, J7 and J14, (see FIG. 5) showed specificity against Jurkat.E6 cells, but did not bind with control Ramos cells. Twenty-four tested sequences from the competitively eluted library either bound to both Jurkat.E6 cells and Ramos cells or did not bind to either cell line. While sequences not binding to either cell line could be nonspecific sequences from the partially evolved cell-SELEX pool, the sequences binding to both cell lines might be targeting receptors common to both cell lines.

The three positive hits were further analyzed. The full-length aptamers J4, J7 and J14 showed variable binding to the Jurkat.E6 cells. During post-SELEX structure-activity relationship studies, it has been shown that truncation of full-length aptamer is desirable to optimize fold and increase affinity. Therefore, in order to maximize the most favorable fold of the aptamer, the 3' and 5' ends of J4 and J14 were systematically truncated for use in later studies. See the truncated forms of J4.1 and J14.1 in U.S. patent provisional application Ser. No. 62/320,793. All three sequences were analyzed for their binding constant against Jurkat.E6 cells. A considerably high Bmax/2 for J14.1 was observed, suggesting that J14.1 approached high specificity, but not affinity, while J4 and J7 showed comparable binding affinities to aptamers generated from cell-SELEX in other reports, suggesting that aptamers J4 and J7 approached the requirements for both affinity and specificity.

The specificity towards the antigen on CD3ε was invested by utilizing competitive binding experiments against anti-CD3ε antibody, which was used in LIGS. Anti-TCRαβ antibody was employed as a control. 50 pmols of aptamer and equal number of pmols of random sequences were incubated with 75,000 cells for 40 min at 0° C. Then, either anti-CD3ε HIT3a clone or anti-TCRαβ antibody in excess was added to allow competitive binding for an additional 40 minutes. Cells were subsequently washed and analyzed for aptamer binding using flow cytometric assay.

With reference to FIGS. 6A to 6I, flow cytometric competitive binding analysis of J4.1, J7 and J14.1 is shown without anti-CD3ε (FIGS. 6A, 6D and 6G), with anti-CD3ε (FIGS. 6B, 6E and 6H) and anti-TCRαβ antibody (FIGS. 6C, 6E and 6I) for each of J4.1, J7 and J14.1. Each FITC-labeled random control or J4.1, J7 or J14.1 (1 µM) was incubated for 40 minutes on ice with $75\times10^3$ Jurkat.E6 cells. Then, binding buffer or anti-CD3ε HIT3a clone or anti-TCRαβ antibody was added and incubated for an additional 40 minutes. The cells were washed with 1.5 mL of wash buffer and the binding of respective aptamer analyzed by flow cytometry. Aptamer fluorescence intensity on X-axis indicates the binding of each aptamer. Thus, increment of fluorescence intensity can be directly compared to baseline random control as an indicator of aptamer binding. Aptamer fluorescence intensity on the X-axis shifted to background when anti-CD3e HIT3a was added to all three aptamers, and binding of J7 and J14.1 was affected when anti-TCRαβ antibody was added. No difference in fluorescence intensity was observed for random control.

Three different patterns of aptamer binding in the presence of either anti-CD3ε or anti-TCRαβ antibody were observed. Aptamer J7 lost binding in the presence of both anti-CD3ε antibody and anti-TCR antibody, possibly because 1) J7 sequence might be binding to a region common to anti-TCR or anti-CD3ε or 2) structural changes were induced by one of the antibodies upon binding to the TCR-CD3 complex resulting a loss of binding of J7. In contrast, aptamer J4.1 only lost its binding when anti-CD3ε antibody was added, suggesting that aptamer J4.1 bound to an antigen unique to anti-CD3ε and that its binding to CD3ε was unaffected by anti-TCRαβ. Aptamer J14.1 showed slightly less binding when anti-CD3ε antibody was present compared to that of anti-TCR antibody. Taken together, all three aptamers showed binding affinity to Jurkat.E6 cells and in the presence of anti-CD3ε, lost their binding suggesting, in turn, that these aptamers bound CD3ε or an antigen close to it. This finding proves that LIGS can be utilized to identify aptamers specific to a predetermined antigen from a multiple-domain receptor complex.

Methods for Example 1

Cell lines, Jurkat.E6 (T lymphocyte) and Ramos (Burkitt's lymphoma), were a generous gift from David Scheinberg lab and Jason Huse lab, Memorial Sloan Kettering Cancer Center. All cells were cultured in RPMI 1640 medium supplemented with 100 units/mL penicillin-streptomycin and 10% fetal bovine serum (heat-inactivated; Invitrogen). Cell lines were validated by flowcytometric assays utilizing antibodies against surface markers uniquely expressed on each cell line.

Buffer compositions: Washing buffer composed of 1×DPBS containing 4.5 g Glucose/1 L and 5 ml of 1M $MgCl_2/1$ L. DNA Binding Buffer (DB) composed of 1×DPBS containing 4.5 g Glucose/1 L, 5 ml of 1M $MgCl_2/1$ L and 100 mg/1 L tRNA. Cell Suspension Buffer (CSB) composed of 1×DPBS containing 4.5 g Glucose/1 L, 5 ml of 1M $MgCl_2$/1 L 100 mg/1 L tRNA and 2 g/1 L BSA.

Phosphoramidites: All of the DNA reagents needed for DNA synthesis were purchased from Glen Research or ChemGenes. All the DNA oligo sequences were chemically synthesized attaching a fluorophore at the 3' end using standard solid phase phosphoramidite chemistry on an ABI394 DNA (Biolytics) synthesizer using a 0.2 μmole scale. Aptamer candidates are synthesized in house using a solid phase DNA synthesizer according to manufacturer's protocol (Applied Biosystems, Inc. Model 394). All DNA synthesis reagents were obtained from Glen Research. The completed DNA sequences were de-protected and purified using HPLC (Waters) equipped with a C-18 reversed phase column (Phenomenex). DNA concentration is determined by a UV-VIS spectrophotometer (Thermo Scientific; Evolution 300) and stored in DNA Binding Buffer (DB) at −20° C.

Cell-SELEX procedure: The PI staining of the cells and flow cytometric analysis of expression of CD3ε utilizing PE labeled anti-CD3ε antibody (BD Pharmingen mouse anti-human) along with an isotype control (mouse IgG1 Biolegend) was performed on a regular basis to maintain high quality cells expressing CD3ε prior to perform each round of SELEX.

The ss-SELEX DNA library DB buffer was heated at 95° C. for 5 minutes and snapped cooled in ice for 30 min prior to selection. Cells were prepared for SELEX experiments by washing three times with the wash buffer; subsequently, re-suspending them in 100 μL of a cell suspension buffer prior to incubation with 100 μL of a ss-DNA library for 40 minutes on ice. The first round of selection was done with 10×10$^6$ cells and 100 nmol of ss-DNA SELEX library.

The supernatant was collected as the unbound fraction. The cells bound to the library were washed with wash buffer (12 mL) to remove weak or nonspecifically bound DNA strands. The bound DNA library was eluted by heating at 95° C. for 10 minutes in 200 μl, DNAse/RNAse free water. A two-step polymerase chain reaction (PCR) was employed for the optimization of the PCR conditions and a large scale PCR was employed to expand the evolved library as reported elsewhere. A double-stranded PCR amplified DNA-library was made single-stranded using avidin agarose beads (Pierce) and desalted using NAP-10 columns (GE) as described by Sefah et. al.[16] For subsequent SELEX rounds, 250 nM of the FITC-tagged ss-DNA library was used from round two to round sixteen.

Ligand-Competition: The enriched 16$^{th}$ library of FITC-tagged ss-DNA cell-SELEX or control zero cycle ss-DNA library was heated at 95° C. for 5 minutes and cooled on ice for 20 minutes. 10×10$^5$ cells were incubated with 250 nM 16$^{th}$ cell-SELEX-round ss-DNA of 25 μl, for 40 minutes in ice and washed twicel mL and 0.5 mL wash buffer. The pre-treated Jurkat.E6 cells with the 16$^{th}$ SELEX-pool were suspended in 50 μL of binding buffer and then incubated with (2.5 μL) of APC mouse anti-human CD3 antibody (BD Pharmingen; cat. no. 555342) 40 min on ice to compete and elute the potential aptamer candidates. Following incubation, the eluted 16$^{th}$ fraction obtained through competition, which is in the supernatant was collected and amplified by PCR. A two-step PCR was performed. First, the whole fraction resulting from LIGS was amplified using 10-PCR cycles. The, second PCR was employed and number of cycles were optimized to obtain adequate yields necessary for the cloning step. To ensure the presence of CD3ε expressed on Jurkat.E6 cells, 10×10$^5$ cells were incubated in parallel with an APC mouse anti-human CD3 antibody (BD Pharmingen; cat. no. 555342) or isotype control (APC mouse IgG1-k, BioLegend; cat. no. 400121). 1 μl antibody/isotype is added per 1×10$^5$ cells and incubated at 4° C. for 30 min in cell suspension buffer. After incubation, all the samples washed and the sample analyzed by FACS Calibur flow cytometry (cytek) by counting 10000 events.

Two different SELEX libraries generated from (1) The DNA pool from the SELEX-16$^{th}$ round specifically enriched against Ramos cells, (2) Competitively eluted fraction of the SELEX 16$^{th}$ round using ligand competition specific for antigens on the CD3ε, were cloned into bacteria using a TOPO TA cloning kit (Invitrogen) and positive colonies were subsequently sequenced by the DNA sequencing core facility at Albert Einstein College of Medicine.

Specificity assays: The bindings of the aptamer sequences were evaluated by incubating Jurkat.E6 cells or Ramos cells (75×10$^3$) with a series of concentrations of FITC labeled aptamer 100 μL of binding buffer on ice for 45 minutes. The cells were then washed with 1.5 mL of wash buffer at 4° C. and reconstituted in 400 μL of wash buffer. The binding of the constructs was analyzed using flow cytometry by counting 5000 events for each concentration.

Determination of the apparent dissociation constant of aptamers: Six different working concentrations of the aptamer and control library is prepared using binding buffer, a sample set of concentrations are given; 1) 1000 nM 2) 500 nM 3) 250 nM 4) 125 nM 5) 20.8 nM 6) 3.46 nM. Cells are prepared for flow cytometry analysis by washing three times with wash buffer. 75×10$^3$ cells are incubated with the each aptamer concentration and random library for 40 min on ice. After washing cells with 1.5 ml of wash buffer the cells are analyzed with FACS Calibur flow cytometer by counting 5000 events. FlowJo software is used to determine median fluorescence intensity for each concentration of aptamer sample and random control. Median fluorescence intensity of random control is subtracted from corresponding median fluorescence intensity of each aptamer concentration. The calculation of Bmax/2 was done using the same method as described in Sefah et al.

Competition assay with individual aptamer molecules: Fluorescently labeled 1 μM aptamer (50 μL) was incubated on ice with 75×10$^3$ Jurkat.E6 cells for 45 minutes. Then anti-CD3ε HIT3a clone or anti-TCRαβ was added and incubated for additional 45 minutes. At the end of incubation, cells were washed with 1.5 mL of wash buffer, and reconstituted in 300 μL of wash buffer, and binding of aptamer and antibody was analyzed on a flowcytometer.

EXAMPLE 2

IgM Expressed on Burkitt's Lymphoma Cells

In this example, an antibody against IgM expressed on Burkitt's lymphoma cells (Ab) outcompeted and replaced the aptamer candidates binding to the same target of the Ab. Based on the specificity of Ab towards its target, the aptamers identified by LIGS showed specificity towards Ab's target. The selected aptamers show specificity towards Ramos cells. As expected, identified specific aptamers for mIgM, competes with the cognate Ab binding to its target.

The conventional cell-SELEX method was first employed against Ramos cells that naturally express high-levels of the desired antigen (mIgM). Cell-SELEX was continued until a partial enrichment of the evolved SELEX library against the target cells was observed. Next, the partially enriched library was divided into fractions. The first fraction was PCR-amplified, cloned and sequenced. These sequences are specific towards target cells. An excess of Ab was introduced on the second fraction, which was pre-incubated with Ramos cells subsequently washed to remove non-binding sequences, to selectively outcompete and elute potential aptamers that bind to the cognate antigen less strongly when the anti-IgM Ab is present. The sequences outcompeted by Ab were PCR-amplified, cloned, sequenced. Finally, sequences obtained from DNA sequencing of two fractions of SELEX pool were aligned using the ClustalX.2 program and based on set criteria, specific aptamer candidates against mIgM in target cells were screened and identified.

Cell-SELEX was carried out without incorporating a negative selection on the assumption that potential aptamer candidates could be partially enriched towards the desired antigen, i.e., mIgM, applying an antibody against the aptamer would elute these sequences, despite the existence of unrelated off-target sequences in the partially-evolved pool. The expression of mIgM on Ramos cell lines was evaluated utilizing anti-IgM antibody. Ten million cells and a high concentration of initial DNA library were employed during the first round of selection to increase the probability of capturing potential "binders". A partial enrichment of the evolved pool was detected starting at round 13 of cell-SELEX pool, compared to the unselected pool. The remaining round 13 was used in LIGS. To elute mIgM-specific sequences, an excess amount of Ab (1 µg) was introduced to compete with the aptamer from fraction of round 13 of cell-SELEX pool pre-incubated with Ramos cells followed by a wash to remove non-binding DNA molecules. The supernatant containing sequences out-competed by Ab were then collected.

To confirm that the Ab had indeed interacted with mIgM, and to investigate Ab's effect on aptamer pool 13 fraction-2 binding to Ramos cells, cells after Ab competition were analyzed by flow cytometry. The binding of the anti-IgM Ab to its antigen on Ramos cells replaces the binding of some aptamer sequences enriched in the evolved pool. This observation suggests that at least a few sequences enriched in the round 13 fraction-2 are eluted by anti-mIgM Ab. Based on the PCR of eluted pool at this step, it was observed that a low number of sequences were eluted during this step, mainly because: 1) the DNA pool was only partially evolved, with a low number of aptamer copies, 2) a low number of cells was employed in the LIGS, 3) Ab competition, which is designed to selectively elute specific sequences, only generates a low number of specific sequences for one target antigen.

Figure 7:
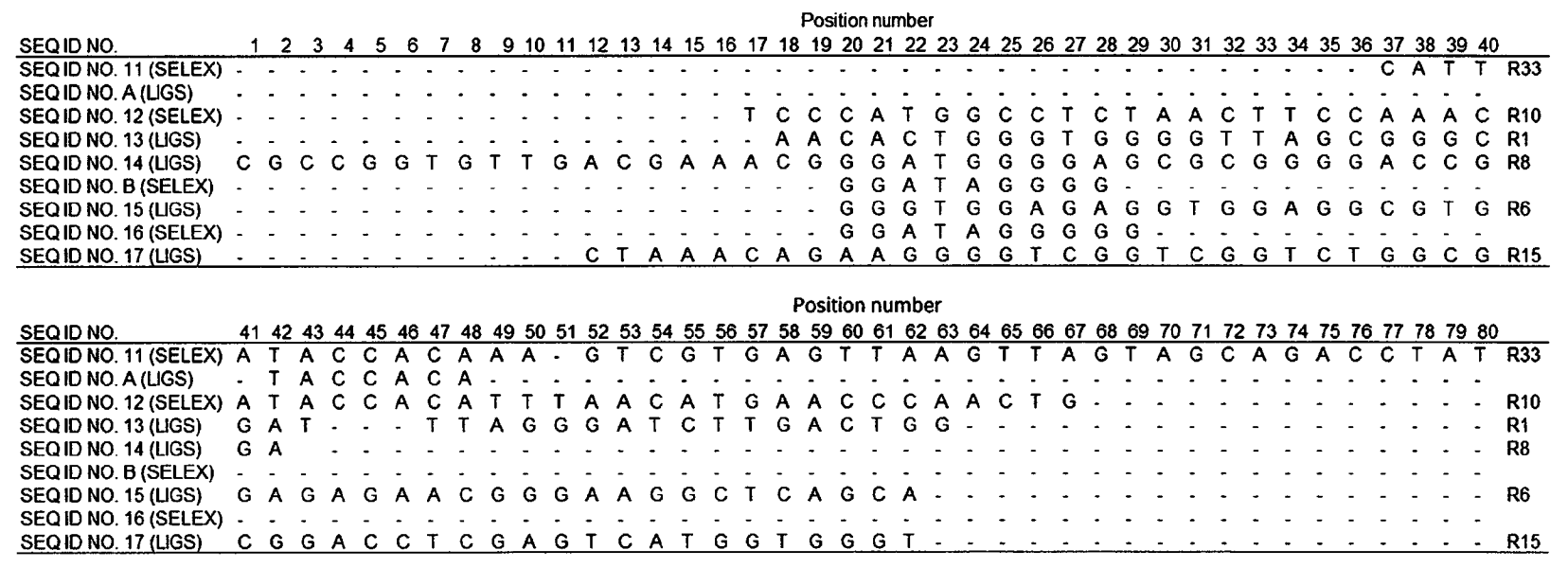

Since the SELEX pool is partially enriched, multiple fractions of round 13 of cell-SELEX pool were cloned, sequenced and competitively eluted fraction of round 13 of cell-SELEX pool. About 500 sequences were obtained from all fractions, which could be categorized into families based on their sequence homology. Without wishing to be bound to any particular theory, it was believed that enriched sequences towards the cell line (Ramos) predominate in the library and have a higher probability in "surviving" the pool. Therefore, the sequences resulting from sequencing of round 13 of cell-SELEX pool would contain all of the sequences that were enriched towards Ramos cells. On the other hand, the sequences obtained from LIGS would favor the set of sequences selectively eluted by the ligand. Analysis of the sequences obtained from sequencing of competitively eluted pool or the cell-SELEX round 13 pool showed two types of sequences: First, sequences share motifs common to sequences in round 13 of cell-SELEX pool and competitively eluted pool; Second, sequences repeated within the competitively eluted library. Both types of sequences that repeatedly appeared within a family with common motifs from both pools or within the competitively eluted pool were selected for further study. For example, as shown in FIG. 7, sequence R10 only appeared on cell-SELEX round 13, however, a shorter version of a common motif was identified to appear in competitively eluted pool. Also, R6, R8 and R1 share a common GGG motif, differing only in few bases within the motif (FIG. 7). The same sequence was observed repeated within the competitively eluted library, and within the main cell-SELEX round 13 pool. Since the scope of this example is to identify sequences specific towards mIgM, even though sequences repeated within the main library might be potential aptamer candidates, the sequences that do not show any common motifs with competitively eluted sequences were not investigated. Based on these criteria thirty three different sequences were synthesized and tested either from competitively eluted library or from the main SELEX-library of round 13. Out of thirty three sequences twenty seven sequences are from competitively eluted library and six sequences share the same motif of that of competitively eluted library but from cell-SELEX round 13 main pool.

Since the LIGS is predominantly aimed at increasing specificity, individual chemically synthesized sequences based on set criteria of sequence selection, were first tested for specificity. Target Ramos cells were used which expresses high levels of mIgM and non-target Jurkat.E6 cells. Since Jurkat.E6 cells are human T-cell leukemia mainly designed to investigate T-cell receptor complex, by definition these cells do not express mIgM, thus, Jurkat.E6 cells are comparable to a cell line that do not express the antigen validates its use as a non-specific cell line. All specificity assays were done using FITC-labeled aptamers, and a randomized DNA sequence used as a control. Interestingly, three types of binding patterns were observed within tested 33 sequences: 1. Sequences do not bind to either Ramos cells or Jurkat.E6 cells, which might be non-specific amplicons in the library, 2. Sequences bind to both Ramos and Jurkat.E6 cells, these sequences might be binding to commonly present Fcγ receptors present in both types cells eluted by the Ab competition, 3. Sequences bind to only Ramos cells but not to Jurkat.E6 cells, which might be specific sequences towards Ramos cells. This suggests that pool resulted from competitive elution does not necessarily contain only specific sequences, and screening of individual aptamer candidates for specificity is desired to identify antigen-specific aptamer candidates. Out of the tested thirty-three sequences three unique sequences (R1, R10 and R15) were identified that show specificity towards Ramos cells.

The sequences that showed specificity towards mIgM-positive Ramos cells were further investigated for binding affinity. Bmax/2 was evaluated for the sequences that showed specific binding. The calculated Bmax/2 for R1, R10 and R15 are in the sub-micro molar range against Ramos cells, suggesting that sequences generated using LIGS show lower affinities. The issue of lower affinities of the identified aptamers could be predominantly because LIGS was applied to a partially evolved SELEX pool, and evolution of sequences was interrupted. Therefore, a partially evolved SELEX pool might contain sequences with lower to moderate affinities. However, the affinity of these aptamers could be further enhanced given their high specificity by post-SELEX modification followed by linear multimerization approaches as described before.

The identified specific aptamer candidates were investigated to determine if each competes with an anti-IgM Ab for the binding site. The validation of the target using competition against the corresponding antibody has been used before. A competition was performed by first pre-incubating Ramos cells with anti-IgM Ab or anti-CD20 Ab for 30 min and subsequent wash. CD20 is uniquely expressed in mature normal B cells, on early developmental stages. CD20 positive B cells are the source of a variety of B-cell neoplasms, including Ramos cells, which is a B-cell Non Hodgkin's Lymphoma. Therefore, anti-CD20 antibody was used as a control to investigate the antigen specificity to further confirm the specificity of the aptamers towards mIgM. Ramos cells pretreated with Ab were then incubated with individual aptamer sequences. Following wash, binding of each aptamer was analyzed using flow cytometry.

FIGS. 8A to 8C depict the results of flowcytometric competitive binding analysis of R1, R10 and R15 in the presence of IgM. Each FITC labeled library (0.4 µM for R1 (FIG. 8A), 0.5 µM for R10 (FIG. 8B) and R15 (FIG. 8C)) was incubated for 60 min on ice with 1×10$^5$ Ramos cells pre-incubated with either anti-IgM (line 812 FIGS. 8D-F)) or anti-CD20 (line 810 FIGS. 8D-F) followed by washing with 3 mL of wash buffer, and subsequently analyzed by flowcytometry. Area 800 illustrates data points for random plus anti-IGHM while line 802 illustrates data points for random plus anti-CD20. Aptamer fluorescence intensity on x-axis is indicative of binding of each aptamer. Thus, increment of fluorescence intensity directly translates into aptamer binding to pre-treated Ramos cells. When the cells are pre-incubated with anti-CD20 (line 806) all three-aptamer show, an increase in fluorescence intensity. However, when the anti-IgM was introduced aptamer binding is diminished (line 804).

As shown in FIG. 8A to 8C, the introduction of anti-IgM Ab diminished the binding of the aptamer for R1 (FIG. 8A), R10 (FIG. 8B) and R15 (FIG. 8C) showed a slight decrease indicated by diminished binding of each aptamer in the presence of anti-IgM but not when anti-CD20 is present in the corresponding histograms. When the cells are pre-incubated with anti-CD20 all three-aptamers show, an increase in fluorescence intensity (line 810) indicating antibody is binding to the cells. Also when anti-IgM antibody binds to cells indicated by increase in fluorescence intensity (line 812)

R1 and R10 showed a substantial competition with anti-IgM based on the diminished aptamer fluorescence intensity compared (FIGS. 8A-C, line 804) Ramos cells pre-incubated with anti-CD20 antibody (FIGS. 8A-C line 806), R15 does not show substantial competition suggesting that binding of R15 might be stabilized by a secondary antigen specific for Ramos cells. The competition with only anti-IgM not with anti-CD20 is a clear indication that R10 and R1 are specific for mIgM.

Each aptamer was also investigated for its ability to block the binding of the anti-IgM. Post-SELEX modification of aptamers is desirable to increase the homogenous fold and to obtain better yields in chemical synthesis. Therefore, in order to further optimize the structure R1 and R 10 were systematically truncated. A truncated version of R1.1 and R10.T1 were used for blocking experiments. Interestingly R1.1 blocked at lower concentrations of anti-IgM, but no significant blockage of the binding of the anti-IgM to Ramos cells was observed at higher concentration of anti-IgM. Also, no significant difference in the binding of anti-IgM was observed when R10.T1 present compared to randomized control. This could be because R10.T1 unable to block the antibody due to its high off rates resulting from lower affinity. Antibodies are bivalent in nature, therefore, the "on" rate of an antibody binding to its antigen is higher and the "off" rate is lower compared to monovalent aptamers. While these kinetic parameters are key factors, the further evaluation of binding kinetics of Ab and its effect on either aptamer displacement or binding to its antigen in biochemical understanding of LIGS.

Similar patterns of molecular recognition of R10 and R1 were observed. These two aptamers investigated to determine if they compete to bind to the same antigen. Unlabeled R1.1 was incubated with excess to fluorescently labeled R10 with Ramos cells. Washing of unbound aptamer followed by flowcytometric analysis revealed that both R1.1 replaces R10 suggesting that both aptamers binding to the same antigen. This evidence further confirms that the aptamers identified utilizing antigen LIGS binding to the same antigen on Ramos cells.

Theoretically, aptamer interactions are specific towards one target; therefore, the set of aptamers generated in the end of the cell-based selection are expected to correlate to the altered levels of molecules in the positive cell line. Using this approach, a number of aptamers had been selected. Aptamers selected using cell-SELEX compete with the cognate antibody for binding to its target antigen. For example, the aptamer TD05, selected using the cell-SELEX method targeting Burkitt's lymphoma, binds to the heavy chain of membrane bound IgM (mIgM) and competes with the anti-IgM antibody, permitting the bound aptamer from the target to be eluted into the solution. Similarly, an RNA aptamer selected against CD71 expressing cells using the hybrid-SELEX method, competes with anti-transferrin antibody. A cell-SELEX selected aptamer against myeloid leukemia, binds to the sialic acid-binding Ig-like lectin protein and competes with its respective antibody. These reported observations suggest that the aptamers can bind to a region of the receptor close to an Ab binding-site. The decrease in aptamer binding when the respective cognate ligand is present can be due to steric hindrance resulting from the large size or high affinity of the ligand, eluting the aptamer; or the structural changes in the receptor protein induced by ligand (Ab) binding. Also, an antibody is bivalent so the affinity is higher than the monovalent aptamers. High affinity of an antibody leads to lower $K_{off}$ and high $K_{on}$ and kinetically favors the competition by the antibody. It has been already shown that aptamers usually bind to ligand binding sites on receptors or active sites of proteins. Therefore, a partially evolved cell-SELEX aptamer library can also be utilized to identify antigen specific aptamers, by simply using a ligand against the desired target to elute the respective aptamer sequences.

In this example aptamers against mIgM were selected. The mIgM molecule is considered as the hallmark of B-cells, plays a major role in B-cell development and is a major player in transformation of B-cell into malignant B-cells. Also, mIgM pays a major role in autoimmune disorders and 95% of human lymphomas originate from B-cells. There is evidence of activated protein kinase stimulated downstream of BCR demonstrating the significance of developing therapeutics against BCR. Currently, there are no successful targeting agents available against mIgM. Three different aptamer candidates with specificity towards mIgM were identified.

Methods of Example 2

Cell culture: All cells were cultured in RPMI 1640 medium supplemented with 100 units/mL penicillin-streptomycin and 10% fetal bovine serum (heat-inactivated; Invitrogen).

Phosphoramidites: All of the DNA reagents needed for DNA synthesis were purchased from Glen Research or ChemGenes. All the DNA oligo sequences were chemically synthesized attaching a fluorophore at the 3' end using standard solid phase phosphoramidite chemistry on an ABI394 DNA (Biolytics) synthesizer using a 0.2 µmole scale. The completed DNA sequences were de-protected and purified using HPLC (Waters) equipped with a C-18 reversed phase column (Phenomenex). All in vitro experiments were performed using a binding buffer composed of DPBS and 4.5 g/L glucose (Sigma-Aldrich) and 5 mM $MgCl_2$, 100 mg/L, tRNA (Sigma-Aldrich), 1 g/L BSA (Sigma-Aldrich). The wash buffer was composed of DPBS with 5 mM $MgCl_2$ and 4.5 g/L glucose (Sigma-Aldrich).

SELEX Primers and Library: Primers and SELEX library was obtained from Sefah K, D Shangguan, X Xiong, MB O'Donoghue and W Tan. (2010). Development of DNA aptamers using Cell-SELEX. Nat Protoc 5:1169-1185. The SELEX library consisting of primers flanked by a 45 nucleotide-randomized region was purchased from IDT DNA Technologies.

Cell-SELEX procedure: The PI staining of the cells and flow cytometric analysis of expression of mIgM utilizing FITC labeled anti-IgM antibody (1 µg, Goat anti human, life technologies) along with an isotype control (1 µg, Goat anti mouse IgG2a, Biolegend) was performed on a regular basis to maintain high quality cells expressing mIgM prior to perform each round of SELEX.

The ss-SELEX DNA library binding buffer was heated at 95° C. for 5 minutes and snapped cooled in ice for 30 min prior to selection. Cells were prepared for SELEX experiments by washing three times with the wash buffer; subsequently, re-suspending them in 100 µL of a cell suspension buffer (cell binding buffer with 2 g/L BSA) prior to incubation with 100 µL of a ss-DNA library for 40 minutes on ice. The first round of selection was done with $10 \times 10^6$ cells and 100 nmol of ss-DNA SELEX library.

The supernatant was collected as the unbound fraction. The cells bound to the library were washed with wash buffer (10 mL) to remove weak or nonspecifically bound DNA strands. The bound DNA library was eluted by heating at 95° C. for 10 minutes in 200 µL DNAse/RNAse free water. A two-step polymerase chain reaction (PCR) was employed for the optimization of the PCR conditions and a large scale PCR was employed to expand the evolved library. A double-stranded PCR amplified DNA-library was made single-stranded using avidin agarose beads (Pierce) and desalted using NAP-10 columns (GE) as described by Sefah K, D Shangguan, X Xiong, MB O'Donoghue and W Tan. (2010). Development of DNA aptamers using Cell-SELEX. Nat Protoc 5:1169-1185. For subsequent SELEX rounds, 250 nM of the FITC-tagged ss-DNA library was used from round two to round thirteen.

Flow cytometric Analysis: The progress of the selection was evaluated utilizing flow cytometric analysis. The PCR amplified DNA library is labeled with fluorescence tag FITC at the 5' end, analyzed by a flow cytometric assay. A 250 nM FITC-tagged ss-DNA library (25 µL) was incubated with $2.5 \times 10^5$ Ramos cells in binding buffer for 40 minutes on ice. After washing twice with wash buffer (3 mL), cells were suspended in 500 µL wash buffer and was analyzed by a FACS Calibur flow cytometer (Cytek,) by counting 10000 events.

Cell binding assays: The affinities of the aptamer sequences were evaluated by incubating Ramos cells ($2.0 \times 10^5$) with a series of concentrations of FITC labeled aptamer 200 µL of binding buffer on ice for 60 minutes. The cells were then washed twice with 1 mL of wash buffer at 4° C. and reconstituted in 400 µL of wash buffer. The binding of the constructs was analyzed using flow cytometry by counting 5000 events for each concentration. The calculation of Bmax/2 was done using the same method as described in Sefah K, D Shangguan, X Xiong, MB O'Donoghue and W Tan. (2010). Development of DNA aptamers using Cell-SELEX. Nat Protoc 5:1169-1185.

The specific binding of each aptamer was evaluated by incubating Ramos cells (0.5 or $1.0 \times 10^5$) and Jurkat.E6 cells (0.5 or $1.0 \times 10^5$) with FITC labeled aptamers of concentrations of 0.5 or 1 µM in a 100 µL of cell suspension buffer on ice for 60 minutes. The cells were then washed twice with 1 mL of wash buffer at 4° C. and reconstituted in 250 µL of wash buffer. Aptamer binding was analyzed using flow cytometry by counting 5000 events for each concentration. As a positive control, a similar assay was performed using an ALEXA FLUOR 647 labeled anti-IgM antibody (1 µg, Goat anti human µ-chain, Life Technologies) along with an isotype control (1 µg, Goat anti human, Biolegend).

Ligand-guided cell-Selection Protocol: Ligand-Competition: The enriched $13^{th}$ pool FITC-tagged ss-DNA pool or control zero cycle ss-DNA pool was heated at 95° C. for 5 minutes and cooled on ice for 20 minutes. $2.5 \times 10^5$ cells were incubated with 250 nM $13^{th}$ SELEX-pool ss-DNA pool of 25 µL for 40 minutes in ice and washed once with 3 mL wash buffer. The pre-treated Ramos cells with the $13^{th}$ SELEX-pool were suspended in 50 µL of binding buffer and then incubated with an ALEXA FLUOR 647 goat anti-human IgM antibody (1 µg) 30 min on ice to compete and elute the potential aptamer candidates. Following incubation, the eluted $13^{th}$ pool obtained through competition, which in the supernatant was collected and amplified by PCR. To ensure the presence of mIgM expressed on Ramos cells, $2.5 \times 10^5$ cells were incubated in parallel with an ALEXA FLUOR® 647 goat anti-human IgM or ALEXA FLUOR® 647 goat IgG Isotype antibody for 30 minutes. After incubation, all the samples washed and the sample analyzed by FACS Calibur flow cytometry (cytek) by counting 10000 events.

Two different SELEX libraries generated from (1) The DNA pool from the SELEX-$13^{th}$ round specifically enriched against Ramos cells, (2) Competitively eluted fraction of the SELEX $13^{th}$ round using antibody competition specific for antigens on the mIgM, were cloned into bacteria using a TOPO TA cloning kit (Invitrogen) and positive colonies were subsequently sequenced by the DNA sequencing core facility at Albert Einstein College of Medicine.

Antigen specificity: Antigen specificity is determined by competition of anti-IgM antibody with aptamers. In order to investigate the competition between anti-IgM (mu) antibody and aptamer, first 0.5 µg/mL of APC anti-human CD20 antibody and 0.25 µg/mL of ALEXA FLUOR® 647 goat anti-human IgM antibody were incubated with $4 \times 10^5$ Ramos cells on ice for 30 min. Then the free antibody was washed with 3 mL of wash buffer, and cells were reconstituted with 400 µl of cell suspension buffer. A final concentration of 0.4-0.5 µM of FITC labeled aptamer or corresponding random control are incubated 125 µL of cell suspension buffer for another 60 min on ice. Then the cells were washed with 1 mL wash buffer and binding events were monitored in FL1 for the aptamer and FL4 for the antibody counting 5000 events using flowcytometry.

Blocking experiments were also conducted with aptamers pre-incubated with antibody. A $10 \times 10^3$ of Ramos cells first incubated with 1 µM of corresponding aptamer or random control on ice for 45 min. Then the pre-incubated cells with the aptamer or random were added to serially diluted concentrations from 20 ng/μL to 0.2 ng/μL of anti-IgM solution and allowed free competition for additional 35 min on ice. Then the cells were washed twice with 1 mL and 0.5 mL wash buffer and re-suspended in 300 μL wash buffer and analyzed the antibody binding with flow cytometry.

To provide proof of principle a method was designed that targeted two receptor proteins. B-cell receptor (BCR) and a T-cell receptor (TCR). To prove the concept a cell line was identified that naturally expresses the membrane receptor of interest as the target cells.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A Ligand-guided-Selection method for screening ligands that are specific to a predetermined antigen, the method comprising sequential steps of:
forming a ligand-cell complex by exposing a culture of target cells to a partially enriched library of ligands, wherein cells in the culture of target cells each have the predetermined antigen, and wherein the partially enriched library of ligands was produced by exposing a library of ligands to the target cells and selecting those ligands that bound, thereby producing the partially enriched library of ligands;
treating the ligand-cell complex with a predetermined ligand that is specific to the predetermined antigen, wherein the predetermined ligand has a molecular weight greater than 200,000 g per mole, the predetermined ligand displacing ligands that are bound to the predetermined antigen to form displace ligands, the step of treating leaving non-displaced ligands bound to the ligand-cell complex;
eluting the displaced ligands;
amplifying the displaced ligands.

2. The method as recited in claim 1, wherein the predetermined ligand is an antibody.

3. The method as recited in claim 2, wherein the predetermined ligand is present in at least a two-fold molar excess relative to the predetermined antigen.

4. The method as recited in claim 2, wherein the predetermined ligand is present in at least a five-fold molar excess relative to the predetermined antigen.

5. The method as recited in claim 2, wherein the predetermined ligand is present in at least a ten-fold molar excess relative to the predetermined antigen.

6. The method as recited in claim 2, wherein the step of amplifying comprises a polymerase chain reaction (PCR).

7. A Ligand-guided-Selection method for screening ligands that are specific to an antigen, the method comprising sequential steps of:
forming a ligand-cell complex by exposing a culture of target cells to a library of ligands, wherein cells in the culture of target cells each have an antigen;
treating the ligand-cell complex with a predetermined ligand that is specific to the antigen, the predetermined ligand displacing ligands that are bound to the antigen to form displace ligands; wherein the predetermined ligand is an antibody with a molecular weight greater than 200,000 g per mole;
eluting the displaced ligands;
amplifying the displaced ligands.

8. The method as recited in claim 1, further comprising:
performing a sequence alignment on first ligands from the partially enriched library of ligands and second ligands from the displaced ligands;
identifying, based on the sequence alignment, a common sequence of nucleotides.

* * * * *